United States Patent [19]

Judell

[11] 4,379,460

[45] Apr. 12, 1983

[54] METHOD AND APPARATUS FOR REMOVING CARDIAC ARTIFACT IN IMPEDANCE PLETHYSMOGRAPHIC RESPIRATION MONITORING

[76] Inventor: Neil H. K. Judell, 509A Lafayette Rd., North Kingston, R.I. 02852

[21] Appl. No.: 188,392

[22] Filed: Sep. 18, 1980

[51] Int. Cl.³ .................................................. A61B 5/08
[52] U.S. Cl. .................................... 128/671; 128/723
[58] Field of Search ............ 128/671, 700, 716, 720, 128/723, 734

[56] References Cited

U.S. PATENT DOCUMENTS

| 3,347,223 | 10/1967 | Pacela | 128/723 X |
| 3,536,062 | 10/1970 | Ham | 128/671 |
| 3,572,317 | 3/1971 | Wade | 128/671 |
| 3,587,562 | 6/1971 | Williams | 128/671 X |
| 3,608,542 | 9/1971 | Pacela et al. | 128/723 |
| 3,742,936 | 7/1973 | Blanie et al. | 128/723 |
| 3,802,419 | 4/1974 | Yates | 128/723 |
| 3,976,052 | 8/1976 | Junginger et al. | 128/671 |
| 4,137,908 | 2/1979 | Degonde et al. | 128/700 X |
| 4,248,240 | 2/1981 | Eykern | 128/671 |

*Primary Examiner*—Lee S. Cohen
*Attorney, Agent, or Firm*—Malin & Haley

[57] ABSTRACT

A method of removing cardiac artifact during monitoring of a patient's respiration using impedance plethysmography when the patient has a regular, substantially periodic heartbeat. This method comprises generating an impedance signal responsive to both cardiac and respiration activity in the patient's chest. The signal is filtered by removing the cardiac activity component due to its substantially periodic character. An output signal is produced from the filter apparatus which is a function of substantially only the patient's respiration rate.

An improved impedance plethysmograph carries out the method substantially as described above.

4 Claims, 4 Drawing Figures

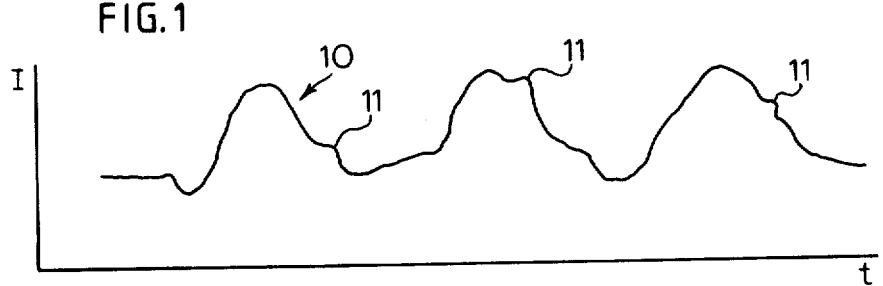
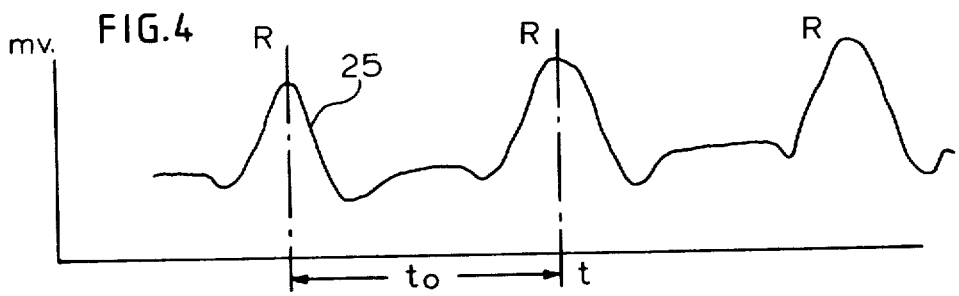
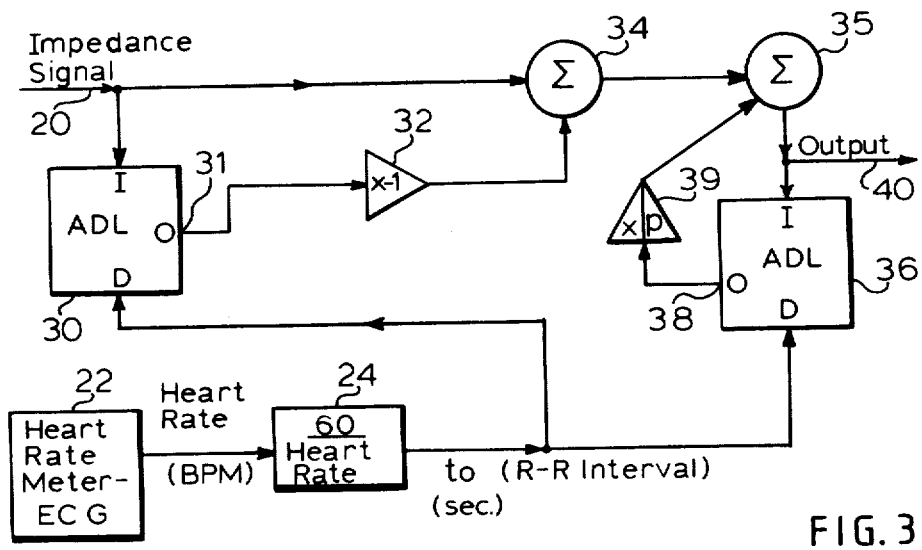

METHOD AND APPARATUS FOR REMOVING CARDIAC ARTIFACT IN IMPEDANCE PLETHYSMOGRAPHIC RESPIRATION MONITORING

BACKGROUND OF THE INVENTION

1. Field of the Invention

The present invention relates to a cardiac artifact removal technique, and more particularly, concerns a method and apparatus for removing cardiac artifact during the monitoring of a patient's respiration using impedance plethysmography when the patient has a regular, substantially periodic heartbeat.

2. Description of the Prior Art

Monitoring the respiration of a patient can be performed electrically by impedance plethysmography. Respiration characteristics of the patient are determined by measuring changes in chest impedance. Respiration produces variations in the shape and content of the patient's chest that are electrically detectable as impedance variations. Electrodes placed on the patient's chest allow these impedance variations to be monitored.

The respiration signal developed through the electrodes essentially is a measure of transchest impedance. In determining the patient's respiration, the impedance variation that is of most significance is a result of change in the volume of air in the lungs. However, inasmuch as the chest and its contents are affected by other activities, the monitored impedance will also be a function of these activities. For instance, any change of blood volume in the chest will cause a change in the impedance signal, as will any change in the chest shape or size such as caused by moving or attempting to breathe with the trachea blocked. Each of these latter activities contributes to the change of impedance. Therefore, the impedance signal which is intended to correlate closely with respiration rate also has these extraneous contributions which basically are undesirable artifacts with respect to pure respiration monitoring.

An abnormal patient movement may be easy to detect and can be readily discarded by the attendant who monitors the impedance changes. However, artifact is also introduced into the impedance signal by varying pleural blood volume, which is caused by the action of the heart in pumping blood during each heartbeat. Since this cardiac activity is ongoing constantly at the same time respiration is being monitored, this cardiac artifact is likely to be present in the signal most of the time. Accordingly, it would be most desirable to be able to eliminate this cardiac artifact due to normal heart activity from the impedance signal so that the signal is almost purely related to the respiration of the patient.

Various respiration monitors have been described in U.S. Pat. Nos. 3,536,062; 3,572,317; 3,802,419; and 3,976,052. However, none of these patented systems provides a technique for removal of cardiac artifact from the impedance signal.

SUMMARY OF THE INVENTION

A method of removing cardiac artifact during the monitoring of a patient's respiration using impedance plethysmography when the patient has a regular, substantially periodic heartbeat comprises generating an impedance signal responsive to both cardiac and respiration activity in the patient's chest. This signal is filtered by removing the cardiac activity component due to its substantially periodic character. An output signal is produced from the filter means which is a function of substantially only the patient's respiration rate.

Another aspect of the present invention is an improved impedance plethysmography apparatus of the type for monitoring respiration of a patient. The known impedance plethysmograph includes means for measuring an impedance signal generated by changes occurring in the patient's chest. The improvement comprises means for removing artifact from the impedance signal caused by cardiac activity in the chest. This means for removing artifact includes filter means which produces an output signal dependent only upon respiration activity in the patient's chest by removing any signals from the output caused by cardiac activity which is substantially periodic in character.

In the preferred embodiments of both the method and apparatus of the present invention as described above, the filter means includes a first analog filter which receives the cardiac and respiration dependent impedance signal as an input signal. A second analog filter is provided in a cascaded, time-delay arrangement with the first filter. The final output signal is a summation of outputs of both filters as a function of respiration activity with respect to time. Each of these analog filters also receives an input signal as a function of heart rate information from the patient. This heart rate information is based on the time interval between peaks of successive heartbeats of a regularly beating, substantially periodic heartbeat. The frequency response of each filter is designed so that the respiration activity of the patient can be recovered from the filtered signal as closely as possible.

As a result of the foregoing structural arrangement and method steps of the present invention, cardiac artifact is removed from the impedance signal during impedance plethysmography. In this respect, the quality of the impedance signal is improved as a more pure measure of patient respiration. This improved impedance signal is therefore substantially independent of heart rate of the patient. With these cardiac artifacts removed, any alarm system which is connected to the impedance plethysmograph may more easily detect apnea by examining signal energy in the filtered signal over the apnea period. The impedance signal sans cardiac artifact will thus be less susceptible to false alarms which normally may have been encountered if cardiac artifact were present in the impedance signal. The filtered signal may also be used to monitor other respiration parameters such as breath rate using the appropriate equipment.

It is appreciated that the invention as described above assumes a regularly beating heart with substantially consistent intervals between peaks of successive heartbeats. It is this periodic nature of the heartbeat which contributes to the removal of the cardiac artifact from the impedance signal. Should the heartbeat be somewhat irregular, it would detract from the purity of the impedance signal as being completely functionally related to patient respiration. However, inasmuch as a regularly beating heart is the norm rather than the exception, the present invention will be applicable in almost all instances where the patient's respiration is monitored by impedance plethysmography.

Moreover, with the time delay nature of the present invention and components of the signal being accumulated before the final output signal is generated, it is readily implemented into a microprocessor-based instrument.

BRIEF DESCRIPTION OF THE DRAWINGS

FIG. 1 illustrates a typical patient respiration waveform monitored by impedance plethysmography with cardiac artifact present;

FIG. 2 illustrates a typical patient respiration waveform monitored by impedance plethysmography with no cardiac artifact present;

FIG. 3 is a block diagram schematically illustrating the functioning of the improved impedance plethysmograph of the present invention in conjunction with a heart rate meter; and FIG. 4 illustrates a typical ECG waveform representing a regularly beating, substantially periodic heartbeat.

DETAILED DESCRIPTION

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, particularly to FIG. 1, there is illustrated a typical waveform 10 which may be generated by an impedance plethysmograph and representing the respiration of a patient. This respiration waveform clearly includes a number of artifacts 11 which likely are caused by cardiac activity in the patient's chest and which produce variations in the impedance which is being measured by the electrodes placed on the patient's chest. If the artifact caused by cardiac activity or otherwise is removed, the respiration waveform would typically assume the shape of waveform 12 as illustrated in FIG. 2. Waveform 12 includes smoothly curved traces thereby omitting the erratic influence which is associated with the presence of artifact. It is the intent of the present invention to remove artifact, especially that associated with cardiac activity, to thereby produce the smooth respiration waveform which would be generated by the patient and monitored during impedence plethysmography.

Referring now to FIG. 3, the block diagram therein schematically illustrates the preferred embodiment of the present invention which removes cardiac artifact in impedance plethysmographic respiration monitoring. An impedance signal 20 is generated from appropriate electrodes placed on the chest of the patient (not shown) in order to measure transchest impedance. Impedance signal 20 which is measured between the electrodes is responsive to changes in the shape and content of the patient's chest. For instance, any changes in the volume of air in the patient's lungs, blood volume in the chest or change in the chest shape or size will induce a change in impedance signal 20. With this in mind, impedance signal 20 if monitored on a display device would appear similar to waveform 10 as depicted in FIG. 1, with artifact 11 being present in the waveform. This, then, is the type of impedance monitoring which is well known and is typical of present day impedance plethysmography.

At the same time transchest impedance is being measured on the patient, standard ECG monitoring is generally going on as well. In this ECG equipment heart rate of the patient is monitored by heart rate meter 22. This heart rate meter will provide an indication of the number of beats per minute that the patient's heart is beating. With respect to the present invention, this heart rate is fed to a processor 24 which determines the time interval, in seconds, between peaks of successive heart beats. Referring briefly to FIG. 4, a typical waveform 25 representing a regularly beating, substantially periodic heartbeat is illustrated. Each peak of the heartbeat is designated as R. The time interval, $t_0$, between the peaks of any two successive heartbeats can therefore be determined in conjunction with heart rate meter 22 and processor 24. The output from processor 24 is therefore $t_0$ as indicated on FIG. 4.

With the recognition that impedance signal 20 carries components of both respiration and cardiac activities, the solution to the cardiac artifact problem can be approached by modeling the problem and then using the appropriate actual elements which the model solution suggests. In such a model, let $c(t)$ be the signal portion due exclusively to cardiac activity, and let $r(t)$ be the signal portion due exclusively to respiration activity. Then the received impedance signal $x(t)$ is given by:

$$x(t) = c(t) + r(t).$$

Assuming a regularly beating heart, with an R to R interval (as illustrated in FIG. 3) of $t_0$ seconds, then $c(t)$ is periodic, so that for all t, $c(t) = c(t - t_0)$. With this in mind, the method for removing cardiac artifact can be accomplished by designing a filter which takes x as its input, producing y as its output such that:

$$y(t) = x(t) - x(t - t_0).$$

substituting the cardiac and respiration activity components for x provides the following:

$$y(t) = [c(t) + r(t)] - [c(t - t_0) + r(t - t_0)].$$

combining like terms provides the following:

$$y(t) = [c(t) - c(t - t_0)] + [r(t) - r(t - t_0)].$$

However, since $c(t)$ equals $c(t - t_0)$, it follows that:

$$y(t) = r(t) - r(t - t_0).$$

Thus, the output of this filter is then wholly dependent only upon the component of activity due to the patient's respiration, therby eliminating any cardiac artifact in the impedance waveform.

In a filter which would remove the cardiac artifact as just described, it is desirable to recover, as closely as possible, the component due solely to respiration activity, $r(t)$. This filter would have a frequency response, $H(\omega)$, as follows:

$$H(\omega) = 1 - e^{j\omega t_0}$$

where $j = \sqrt{-1}$ and $\omega$ is frequency. Therefore, in order to recover $r(t)$, in the ideal circumstance a second filter would be cascaded with the first filter. This second filter would have a frequency response as follows:

$$K(\omega) = 1/[1 - e^{j\omega t_0}].$$

Unfortunately, stability requirements prohibit a second filter with this kind of frequency response. However, the filter can be fabricated with a frequency response as follows:

$$K(\omega)=1/[1-pe^{j\omega t_0}]$$

where p is a constant greater than or equal to zero, but less then 1. This filter arrangement is known as a "notch filter," and p is the parameter which controls the sharpness of the notches. The closer p is to 1, the sharper the notch.

The filter arrangement to carry out the cardiac artifact removal from a regularly beating, substantially periodic heartbeat is illustrated in FIG. 3. A first analog filter element 30 receives two inputs, one from the impedance signal 20 and the other from the heart rate processor 24 which corresponds to the R to R interval representing $t_0$ in seconds. Filter element 30 is essentially an analog delay line (ADL) which then generates an output 31 that effectively filters out the portion of the impedance signal which is due to cardiac activity so that its output conforms to the relationship set forth above, namely $y(t)=r(t)-r(t-t_0)$. Output 31 is passed through amplifier 32 which provides a gain stage of $-1$. Both impedance signal 20 and output 31 from filter 30 are then directed to a summing element 34. In order to recover the value of the respiration component r(t) as closely as possible, this signal is then passed through another summing element 35 and into a second analog filter element 36. With filter element 36 being arranged in a time-delay configuration with respect to filter element 30, and inasmuch as it receives as its input the summation of data from summing element 35 (acting on information previously fed to it), this cascaded arrangement will provide for the recovery of the respiration dependent signal, r(t). In addition to the input from summing element 35, second filter 36 is also fed the heart rate output in terms of the R to R interval, $t_0$ in seconds. As in first filter element 30, second filter element 36 is essentially an analog delay line (ADL), and generates an output 38 for feedback purposes to the second filter element. Output 38 is amplified by amplifier 39 before being directed to summing element 35. In order to remove the component of cardiac activity from the respiration waveform while at the same time recovering as closely as possible the component related to respiration activity, the frequency response of filter element 30 is as follows:

$$H(\omega)=1-e^{j\omega t_0}.$$

The frequency response of second filter element 36 is as follows:

$$K(\omega)=1/[1-pe^{j\omega t_0}]$$

where p is a constant greater than or equal to zero, but less than 1. In these frequency response relationships, $j=\sqrt{-1}$, and $\omega$ is frequency. Amplifier 39 is designed so that it has a gain stage equal to the parameter "p" set forth in the frequency response relationship of the second filter element. Generally speaking, if p equals one, the second filter in the system would become unstable. On the other hand, if p equals one, then reconstruction of the respiration waveform would be perfect. Therefore, p should be as close to one as possible to provide the closest representation of the resultant filtered respiration waveform, while maintaining the stability of the second filter in the system.

As a result of this filter arrangement, the final output 40 provides an impedance signal which is a function of substantially only the patient's respiration rate, with the signal now being devoid of any component of cardiac activity. This output from the filter arrangement would then produce a waveform representing the respiration of the patient similar to waveform 12 illustrated in FIG. 2.

In most instances the filter arrangement described herein will be able to produce the waveform such as illustrated in FIG. 2 especially if the heartbeat of the patient is regularly beating in a periodic rhythm. It should be pointed out that this filter arrangement may eliminate the component of the signal related to respiration if the respiration rate of the patient is approximately equal to the heart rate. However, this problem is not expected to occur frequently since the breath rate in a normal patient is approximately fifteen (15) breaths per minute while the heartbeat in a normal patient may be somewhere between sixty (60) and ninety (90) beats per minute.

Thus, the present invention provides a technique for removing cardiac artifact in impedance plethysmographic respiration monitoring so that the impedance signal is most closely associated with only the respiration of the patient.

What is claimed is:

1. In an impedance plethysmographic apparatus of the type for monitoring respiration of a patient including means for measuring an impedance signal generated by changes occurring in the patient's chest, wherein the improvement comprises:
    means for removing artifact from the impedance signal caused by cardiac activity in the chest including;
    filter means which produces an output signal dependant only upon respiration activity in the patient's chest by removing any signals from said output signal caused by cardiac activity which is substantially periodic in character, said filter means receives as input an impedance signal which is a function of both cardiac and respiration activity, said filter means adapted to filter said input impedance signal so that said output signal is a function of only respiration activity,
    a first rate means for providing a heart rate signal to said filter means,
    said filter means including;
    a first analog filter means for receiving said impedance signal as input, and
    a second analog filter means for providing said output signal, said second analog filter means arranged in a cascaded, time-delay arrangement with said first filter means,
    said output signal being a summation of outputs of said first filter means and said second analog filter means as a function of respiration activity with respect to time.

2. The apparatus of claim 1 wherein:
    both said first filter means and said second analog filter means receive said heart rate signal as a function of heart rate information from said patient based on the time interval between peaks of successive heartbeats of a regularly beating, substantially periodic heartbeat.

3. The apparatus of claim 2 wherein the frequency response of said first filter means is represented by the following relationship:

$$H(\omega) = 1 - e^{j\omega t_0}$$

wherein $j = \sqrt{-1}$, $\omega$ is frequency and $t_o$ is said time interval between peaks of successive heartbeats; and wherein the frequency response of said second analog filter means is represented by the following relationship:

$$K(\omega) = 1/[1 - pe^{j\omega t_0}]$$

wherein p is a constant having a value greater than or equal to zero, but less than 1.

4. A method of removing cardiac artifact during the monitoring of a patient's respiration using impedance plethysmography when said patient has a regular, substantially periodic heartbeat comprising:

generating an impedance signal response to both cardiac and respiration activity in the patient's chest, a cardiac activity component generated as part of said signal, filtering said signal by removing said cardiac activity component due to its substantially periodic character to produce a filtered signal; and producing an output impedance signal from said filtered signal which is a function of substantially only the patient's respiration activity, monitoring the patient's heart rate and providing a rate signal which is based upon the time interval between peaks of successive heartbeats of a regularly beating, substantially periodic heartbeat, said filtering includes passing said signal to a first analog filter whose output is cascaded to a second analog filter, both of said filters also receiving as an input signal the patient's heart rate signal, the output from said filters being a function of substantially only the patient's respiration activity.

* * * * *